United States Patent [19]

Kagan et al.

[11] Patent Number: 5,443,072
[45] Date of Patent: Aug. 22, 1995

[54] MINIATURE DISPOSABLE BLOOD FLOW MONITOR

[76] Inventors: Andrew Kagan, 101 Prospect Ave., Hackensack, N.J. 07601; Gerald P. Selden, 36 Mt. Herman Rd., Blairstown, N.J. 07825; James C. Wickstead, No. 5 Cold Hill Rd., Mendham, N.J. 07945

[21] Appl. No.: 184,690

[22] Filed: Jan. 21, 1994

[51] Int. Cl.6 .......................................... A61B 5/0265
[52] U.S. Cl. ...................................... 128/691; 128/687
[58] Field of Search ................ 128/668, 672, 687–691

[56] References Cited

U.S. PATENT DOCUMENTS

| | | | |
|---|---|---|---|
| 3,847,142 | 11/1974 | Williams, Jr. et al. | |
| 4,185,621 | 1/1980 | Morrow | 128/672 |
| 4,409,983 | 10/1983 | Albert | 128/690 |
| 4,938,228 | 7/1990 | Righter et al. | 128/690 |
| 5,033,472 | 7/1991 | Sato et al. | 128/691 |
| 5,101,829 | 4/1992 | Fujikawa et al. | 128/687 X |
| 5,190,047 | 3/1993 | Odagiri et al. | 128/687 |
| 5,205,293 | 4/1993 | Ito et al. | 128/691 |
| 5,247,944 | 9/1993 | Hirano et al. | 128/687 X |

*Primary Examiner*—Angela D. Sykes
*Attorney, Agent, or Firm*—Louis Weinstein

[57] ABSTRACT

A small, lightweight, disposable blood flow monitor adhered directly to the skin of a patient above the vessel being monitored, such as an artery. A transducer generates an electric signal representative of a deflection of a vessel wall due to pulsatile pressure, which deflection is enhanced by a thin conductive substrate providing a mechanical advantage for the detected deflection. Control circuitry periodically stores a peak value of a deflection caused by a systolic pulse. A reference value is obtained by pressing a calibrate switch to store a value representing a systolic pulse encountered during a calibration interval. Peak values of systolic pulses are stored at predetermined intervals and compared with the reference value. A simplified display, preferably comprised of LEDs of different colors respectively represent a normal, slightly abnormal and significantly more abnormal conditions. The monitor, once turned on, remains on throughout its useful operating life. The reference value may be selected or reselected at any given time. The monitor may be comprised of custom circuitry or may utilize a microprocessor having a stored operating program.

23 Claims, 7 Drawing Sheets

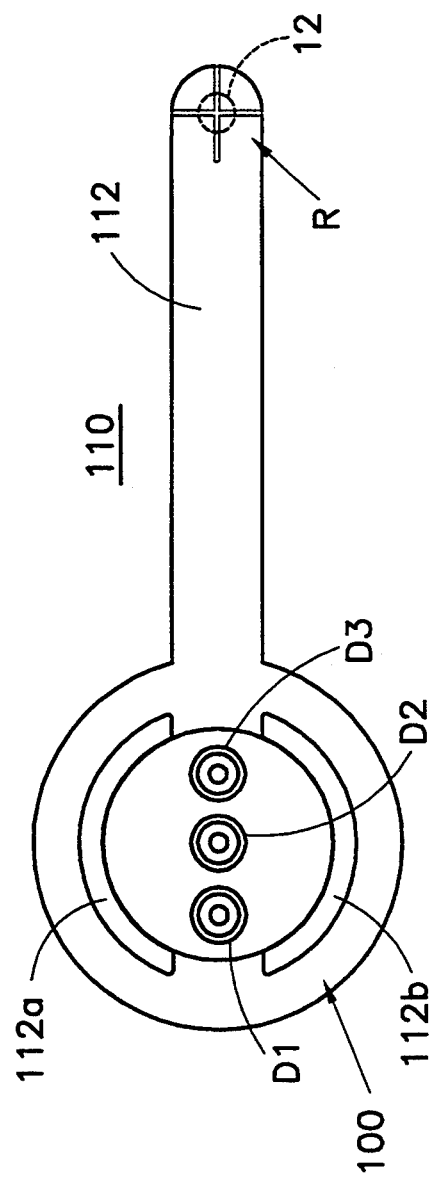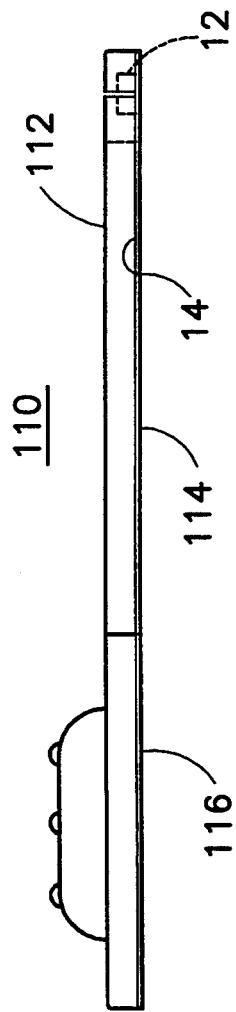
Fig. 5a
Fig. 5b

MINIATURE DISPOSABLE BLOOD FLOW MONITOR

FIELD OF THE INVENTION

The present invention relates to blood flow monitors and more particularly to a novel, miniature, disposable blood flow monitor for measuring displacement of arterial walls against a preset displacement value established by the user during a presetting operation initiated by the user.

BACKGROUND OF THE INVENTION

A number of applications exist wherein it is desirable to monitor blood flow and especially in those situations wherein the patient is ambulatory. It is thus desirable to monitor blood flow with insignificant or minimal interference with a person's normal activities and especially avoiding the necessity of weighing a person down with heavy, bulky and/or clumsy monitoring devices which interfere with typical daily activities, as well as persons confined to bed.

It is further desirable to provide a device which, in addition to being small in size, is of a simplified design to assure accuracy and ruggedness and which utilizes the least complicated method for detecting blood flow rate which is non-invasive and is disposable and hence is inexpensive in design and manufacture in order to meet the cost requisites making it practical to dispose of a monitor after a single use.

BRIEF DESCRIPTION OF THE INVENTION

The present invention is characterized by comprising a disposable blood flow monitor which measures the proportional flow rate of blood in an artery by measuring the displacement of the arterial walls due to the pulse pressure created by the pumping of the heart.

The system compares a preset value of vessel wall displacement with a present value, the difference being displayed in an easily readable manner as a visually readable change in color to indicate normal, cautionary and abnormal regions wherein the regions are represented, for example, by green, yellow and red lamps to represent the three possible states or alternatively a normal and abnormal region wherein two colors, such as green and red, represent the two possible conditions. More specifically, a green lamp indicates no change or a change of less than twenty percent value, a yellow lamp indicates a change of less than sixty percent but greater than twenty percent, and a red lamp indicates a change in value greater than sixty percent.

The present invention is characterized by comprising a small piezo-ceramic crystal having an operating frequency of the order of four kilohertz or greater. The crystal is mounted upon a small, bendable, metallic plate, such as a brass plate, which serves the multiple functions of providing a rugged and firm support and mount for the fragile crystal, providing an electrical contact for the back of the crystal and providing a mechanical advantage which amplifies deflections to enhance the signal created by the crystal.

The crystal produces a static electric field proportional to distortion (i.e. bending) experienced by the crystal lattice.

The crystal signal is amplified by an amplifier comprised of an FET employed in conjunction with a standard transistor amplifier to provide satisfactory gain. A signal is applied to a low pass amplifier having a pass frequency of the order of 100 Hertz.

The output from the low pass amplifier is coupled in common through another amplifier stage to a peak detector and Schmitt trigger.

The peak detector includes a sample-and-hold circuit which holds the peak value of the signal applied thereto and in turn couples the peak signal to a set of differential amplifiers and to a comparator.

The Schmitt trigger generates a square pulse output representative of the presence of a pressure pulse which is applied to a logic gate. The logic gate is initiated by a calibration initiation switch operated by the user. When the switch is held down for at least five seconds, the logic circuit, which further includes delay means, opens a second gate which passes clock pulses from a master clock to a binary counter which is initially reset by closing of the second gate and accumulates a count at a rate determined by the master clock.

A resistor network coupled to the binary counter applies the analog output to a comparator which compares the increasing analog output to the peak value stored by the peak detector. When a comparison occurs, the aforementioned second gate closes and the count of the binary up counter is retained. The analog output of the D to A converter (i.e. resistor network) is compared against peak values by means of the aforementioned set of differential amplifiers and logic circuits. More particularly, the stored value is repeatedly compared against a peak value which, by way of a timing circuit employed as part of the peak detector circuit, resets the peak detector and successively stores a new peak value at regular intervals, such as, for example, every five seconds. The selected intervals are "factory adjustable" by adjustment of a timing circuit. The output is highly simplified to facilitate reading and understanding of same by the user and may, for example, include green, yellow and red lamp indicators, such as LEDs, to indicate, for example, that the measured pulse value is greater, slightly less or significantly less than the stored value. If the value measured is less than a preset margin below the stored value, the yellow lamp will begin blinking and a lower value below the margin from the stored value will cause only the red light to blink. Blinking occurs at the patient's pulse rate.

If the measured value is extremely low, none of the LEDs will be blinking, which indicates very little or no blood flow or that the battery is exhausted.

Recalibration is possible at any time by holding down the calibrate switch for a minimum duration of five seconds to enable the timed gate logic to initiate accumulation of another stored value.

The disposable blood flow monitor is an electronic solid-state module which is quite small. The module is encapsulated in a flexible silicone. The module is attached to the patient through the use of an adhesive gel applied to one surface thereof. The module makes contact with the patient's skin above the artery to be monitored. Pulsations of the artery cause the substrate, which in one preferred embodiment is in the shape of a disc, to be compressed and flexed.

The custom hardware design described hereinabove may be replaced by a microprocessor-controlled design in which the sample-and-hold, switching clock functions, and logic are all performed within the microprocessor, reducing the complexity of the circuit and component count which, in turn, reduces size and overall cost of the disposable device.

The microprocessor-based embodiment utilizes the same disc mounted crystal whose conditioned signal is converted by an internal analog-to-digital converter, digitally stored and then compared to other inputs. The pulse is taken from the same input and the LEDs are directly driven by the microprocessor. The battery "ON" switch is the same as that employed in the custom hardware design and the calibrate initiate button is directly coupled to the processor, reducing the device to only a few components having an estimated current consumption of less than one milliampere.

OBJECTS OF THE INVENTION

It is, therefore, one object of the present invention to provide a small, inexpensive, disposable blood flow monitor which is easy to position, operate and read.

Still another object of the present invention is to provide a novel blood flow monitor which is inexpensive, disposable and which stores a blood value utilized to continuously compare blood flow rate at regular intervals with the stored value to provide an easy-to-read output.

Still another object of the present invention is to provide a novel blood flow monitor which is inexpensive, disposable and which stores a blood flow value that is utilized to continuously compare blood flow rate at regular intervals with the stored value to provide an easy to read output and wherein the stored blood flow rate is easily set and is also easily resettable by the user.

Still another object of the present invention is to provide a blood flow monitor which is inexpensive, small in size and easy to use and which utilizes a small and yet effective converter for converting physical movement into electrical energy, said converter being mounted upon a thin metallic substrate which serves the multiple functions of providing a substrate which contributes structural strength to the converter, serves as an electrode, provides a mechanical advantage which multiplies and strengthens the pulsing condition sensed by the converter and which serves as a mount for the control circuitry.

The above, as well as other objects of the present invention, will become apparent when reading the accompanying description and drawings, in which:

BRIEF DESCRIPTION OF THE FIGURES

FIGS. 2-1 and 2-2, taken together, shows a detailed schematic diagram of the blood flow of FIG. 1.

FIGS. 5a, 6a, 7a and 8a show top plan views of alternative embodiments of the monitor of either FIG. 1 or FIG. 3, for example, incorporating and encapsulating all of the components shown in FIG. 1.

FIGS. 5b, 6b, 7a and 8b show respective side elevations of the alternative embodiments of FIGS. 5a, 6a, 7a and 8a.

DETAILED DESCRIPTION OF THE INVENTION AND PREFERRED EMBODIMENTS THEREOF

Figure 1:
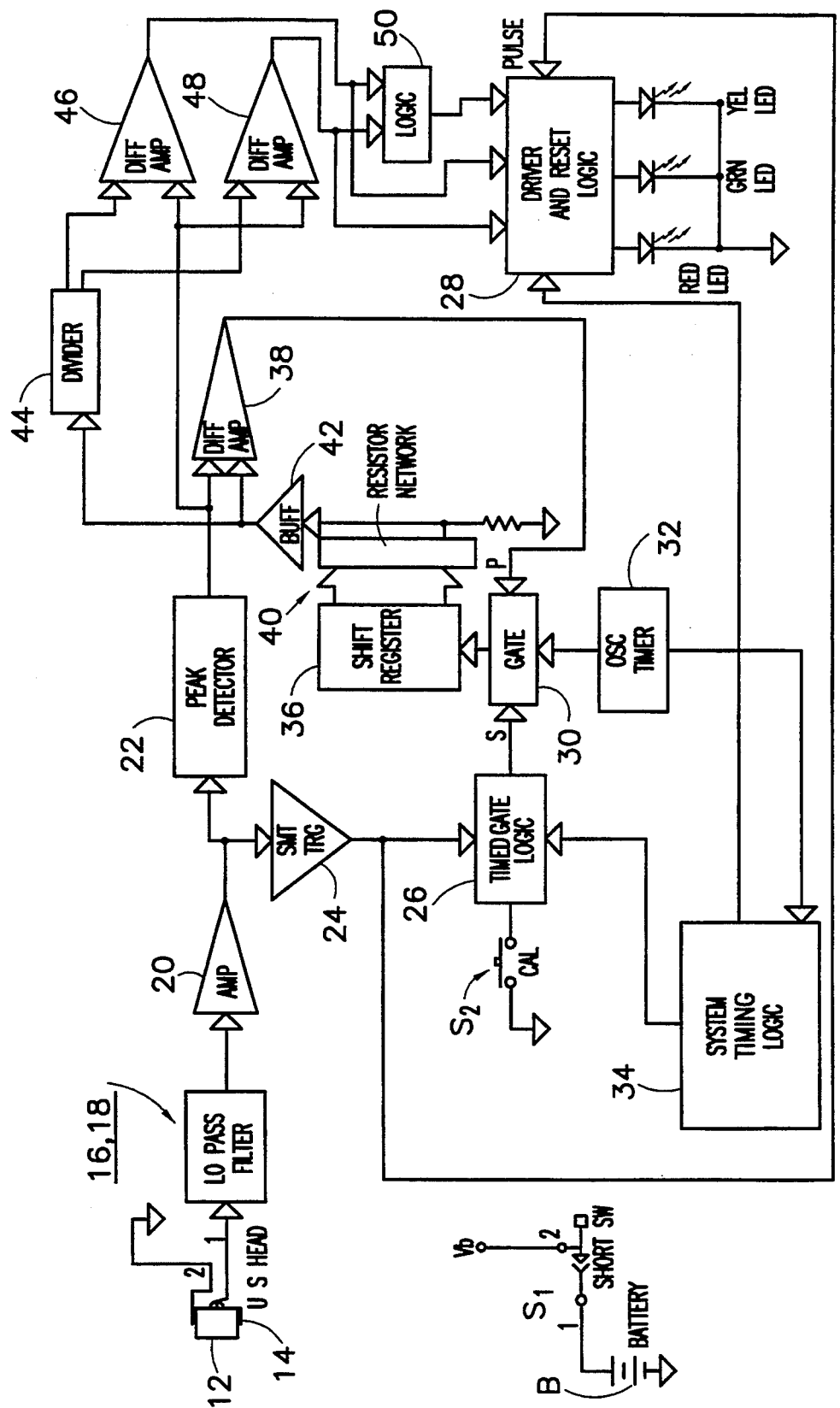
FIG. 1 is a block diagram of a blood flow monitor designed in accordance with the principles of the present invention.

FIG. 1 shows a block diagram of a blood flow monitor 10 embodying the principles of the present invention and comprised of a piezo-elastic transducer 12 which may, for example, be a thin, lead-zirconate-titanate unimorph piezo-ceramic disc which is preferably electrically polarized in the 33 direction. Transducer 12 is mounted upon a small metallic conductive plate such as, for example, a brass plate 14 which serves as the mount and provides firm supporting strength for the fragile crystal as well as providing an electrical contact for the back of the crystal and further providing a mechanical advantage by amplifying the deflection experienced by the monitor. The brass plate, in one preferred embodiment, is a circular-shaped member having a diameter of the order of 1.14 inches and a thickness of the order of 0.005 inches. Transducer crystal 12 produces a static electrical field proportional to the amount of crystal lattice distortion (i.e. bending) experienced by the crystal.

The bottom surface of the monitor is coated with an adhesive for placement on the skin of a patient. One suitable adhesive, for example, is Hydrogel, which is protected by a release sheet that is removed preparatory to placement at a location on the patient where the monitor may be easily mounted and adhered. The location upon the surface of the skin is preferably directly over an artery whose blood flow is to be monitored. The monitor may, for example, be utilized by a patient who has received an artery replacement and it is desired to monitor the blood flow of the affected artery.

The monitor in the preferred embodiment is designed as a single-use, disposable device employing a system battery which may, for example, be a three (3) volt lithium battery having a shelf life in excess of ten years. When the monitor is placed in use, an activate switch S1 is closed connecting the battery to all of the internal circuitry. Once activated, the device in the preferred embodiment cannot be deactivated and will continue to operate until the battery is exhausted. The typical operating life is of the order of forty-eight hours from activation. Switch S1 is preferably designed to have a bendable locking member ML which bends in the direction shown by arrow A as switch S1 is depressed against the bevelled surface. As soon as the switch clears the bevelled surface, locking member ML snaps back into the upright position maintaining switch S1 in the closed position. The battery 3 powers all of the circuitry of monitor 10. Any other suitable design arrangement may be employed in order to maintain the switch closed throughout the operating life of the device.

Whereas the transducer 12 can create large signal levels, the signals are not very powerful. In addition, the transducer 12 has a large capacitance. To properly amplify the signal developed by the transducer, an amplifier with high input impedance and relative immunity to a high capacitance input is utilized to boost the signal from the transducer from approximately 20 mV to 200 mV (a gain of the order of ten). The output impedance of amplifier 16 matches the input impedance of a low pass filter 18 which has a pass frequency of the order of 95 Hertz to insure the measurement obtained by the device is limited to the systolic pressure wave.

Since the low pass filter amplifier diminishes the amplitude of the signal, another amplifier stage 20 is included to boost the signal to a level compatible with the operating characteristics of the remaining electronics.

Amplifier 20 is coupled to the inputs of a peak detector circuit 22 and a Schmitt trigger circuit 24.

A Schmitt trigger 24 converts the analog pressure wave appearing at the output of amplifier 20 into a square wave at logic levels compatible with the electronic circuitry coupled thereto. The output of the Schmitt trigger serves as a control signal applied in common to a time gate logic circuit 26 and a driver and reset logic circuit 28. The signal provided to circuit 28 causes a selected one of the LEDs, LED-1, LED-2 or LED-3 to blink in synchronism with the user's pulsatile pressure, as will be more fully described hereinbelow.

Peak detector circuit 22 measures and stores the peak voltage from transducer 12 which represents the deflection of the arterial wall. As blood flow decreases and the arterial wall deflection decreases, the peak voltage decreases. Nevertheless, the peak value is retained, as will be more fully described.

When a calibrate switch S2 is depressed and held down for at least five seconds, at least one and typically several pressure pulses will be generated even at low rates which are typically fifty pulses per minute. After a five second delay upon closure of calibrate switch S2, timed gate logic circuit 26 closes to initiate a start pulse for closing gate 30 which enables pulses to be passed from the master oscillator 32 and system timing logic circuit 34 through gate 30 to a binary up counter 36 (which may be a shift register) which is automatically reset and starts to accumulate a count determined by the master oscillator and system timing logic. The internal master oscillator may operate, for example, at the rate of one kilohertz. The output frequency of oscillator 32 may be directly coupled to gate 30 or divided down from a higher frequency source (not shown) to a suitable lower frequency, if desired.

Peak detector 22 is preferably comprised of a sample-and-hold amplifier circuit which includes a fast charge capacitor circuit having a very low discharge rate, coupled with a buffer amplifier. Detector 22 stores the peak voltage detected until discharge by a bifet switch circuit forming part of the peak detector, as will be more fully described. The peak voltage is buffered so that coupling of the measured value to another circuit will not discharge the stored value. The buffered output is applied to a bifet switch for measurement and storage of the reference value.

The peak value stored by peak detector 22 is applied to comparator (i.e. difference amplifier) 38. As was mentioned hereinabove, gate 26 closes gate 30 when a square pulse from Schmitt trigger 24, closure of calibrate switch S2 and a pulse from oscillator 32 are applied thereto, causing gate 30 to pass pulses from oscillator 32 to binary up counter 36 which is reset and begins to accumulate clock pulses. The digital output of counter 36 is converted into analog form by a digital to analog circuit 40 which may, for example, be a resistor network. The analog voltage developed by circuit 40 is coupled through buffer 42 to divider circuit 44 and comparator 38. When the increasing analog voltage applied to one input of comparator 38 by buffer 42 is equal to the voltage applied to the other input of comparator 38 by peak detector 22, comparator 38 closes gate 30 preventing the accumulation of further clock pulses and thereby storing the reference value in counter 36.

The analog level appearing at the output of circuit 40 and applied to divider 44 by buffer 42 is divided by a voltage divider circuit to apply different reference level values to respective inputs of a pair of differential amplifiers 46 and 48 which compare the high/low reference levels developed by divider circuit 44 with each new peak value which is sampled and stored by peak detector 22. For example, when the sample level from circuit 22 is greater than the stored reference level, differential amplifier 46 enables LED-1 to light. When the peak level sampled by circuit 22 is less than a predetermined low margin, differential amplifier 48 enables LED-3 to light. Logic circuit 50 causes LED-2 to illuminate when the peak level stored by circuit 22 is greater than the aforementioned low margin but less than the reference value. Schmitt trigger 24 provides a pulse to driver and reset logic circuit 28 to reset and initiate a new lamp illumination upon the occurrence of each pulsatile flow through the artery being monitored.

The blood flow monitor is designed to remain attached to the patient's skin for at least forty-eight hours. Attachment is such that deflections caused by external forces will not alter the position relative to the blood vessel being monitored. The attachment should also include an acoustic coupling medium which will be stable for the amount of time that the monitor unit is attached. One suitable coupling medium comprises a sheet provided with a pressure sensitive adhesive on both major surfaces, which adhesive is preferably an adhesive gel which has acoustic characteristics compatible with acoustic characteristics of human skin and which will not dry out during the period of normal use. One such material is sold under the registered trademark HYDROGEL.

In order to achieve maximum operating time, the monitor unit should be activated just prior to attachment to the patient. Activation of switch S1 is accomplished by operating the switch, which is preferably a semi-hidden power switch, by means of a pen/pencil point or any other device having a fine point. Verification that the unit is turned on and operating properly is checked by lightly squeezing the sensor end of the unit causing the green light (LED-1) to illuminate in synchronism with the squeezing.

One manner of positioning and application of the blood flow monitor is to probe the patient with an independent ultrasonic Doppler device and carefully mark the best placement position on the skin of the patient with a suitable symbol such as "+". The sensing portion of the disposable monitor is placed over the mark using the "+" reference mark R provided on the disposable monitor. As another alternative, the patient may be probed with the disposable monitor unit until a satisfactory site is located and the sensing end of the monitor 10 is attached at that location.

Once the sensor end is positioned and adhered to the skin, the remainder of the monitor is attached to the skin, being careful not to stress the sensor end so as to cause bending, twisting or pulling of the connection between the sensor end and the indicating end of the monitor.

The calibration technique which has been set forth hereinabove merely requires that the patient depress the calibration switch S2 for a continuous period of at least five seconds. The arterial deflection amount will be stored and a positive indication of storage of the reference value is the blinking of LED-1 which will occur in synchronism with the patient's pulse to verify that there is adequate blood flow. Before calibrating monitor 10, it is preferable to measure blood flow with a standard ultrasonic blood flow meter.

Figures 1, 2:
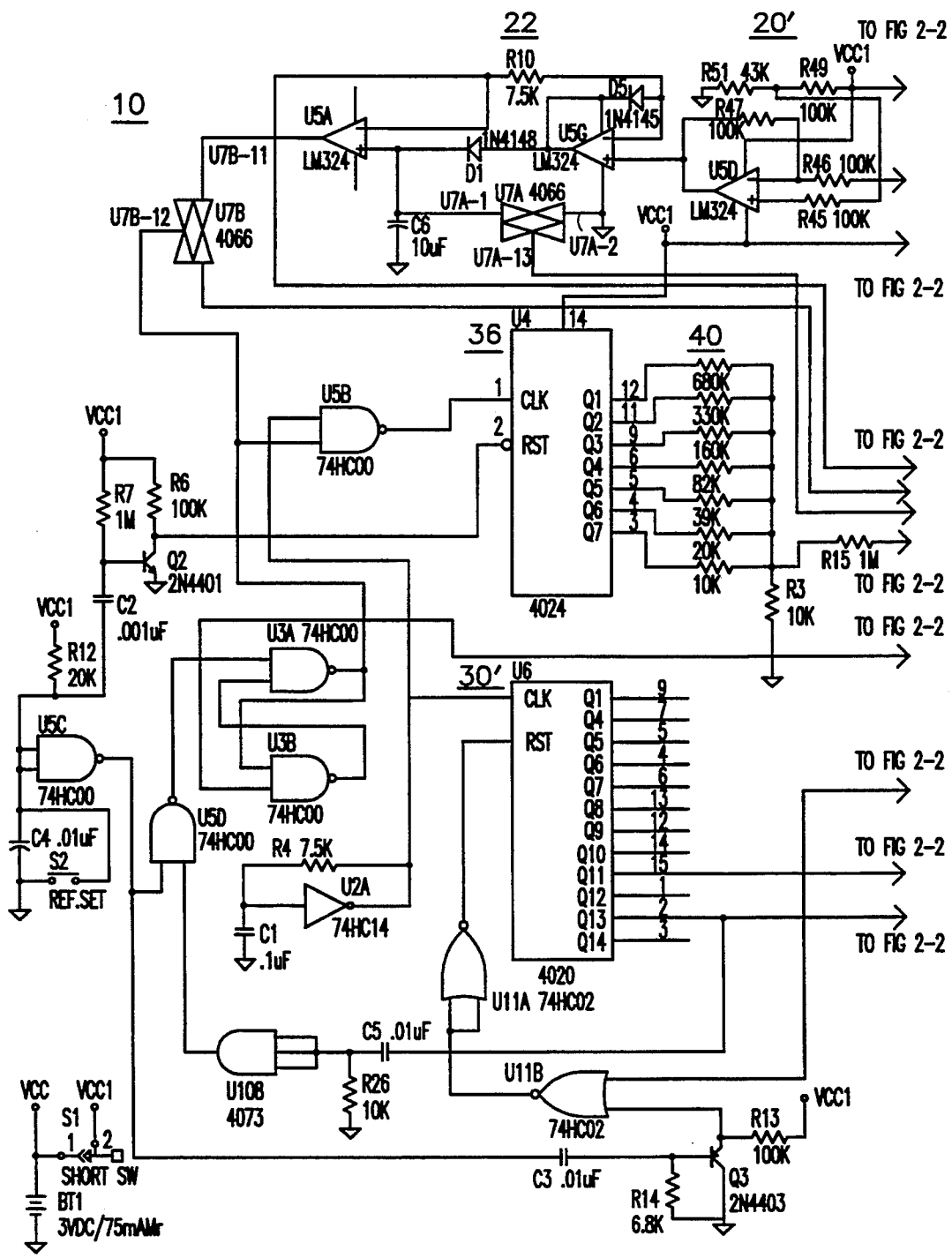
Figure 2:
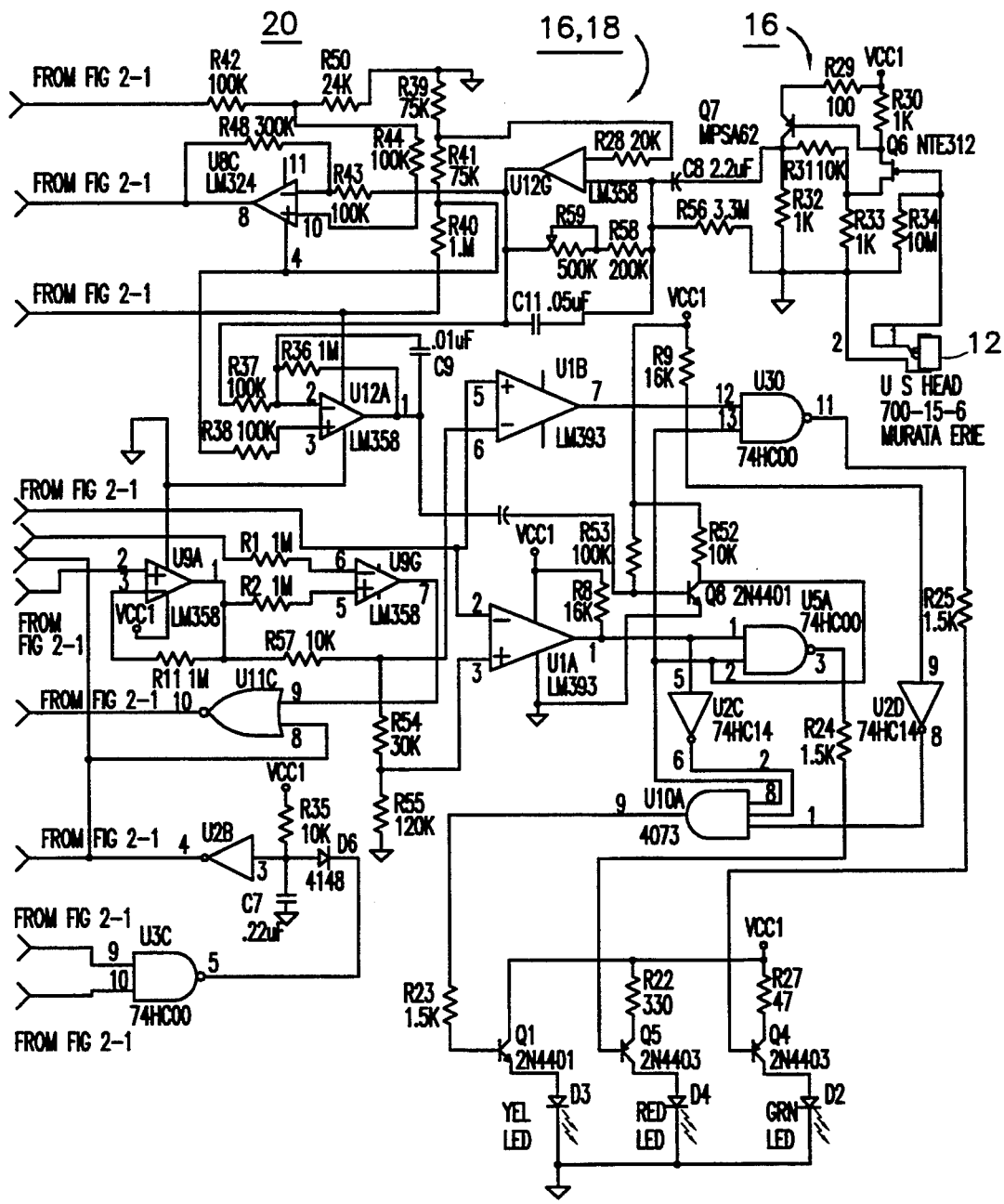

FIGS. 2-1 and 2-2, taken together, show the detailed schematic of the embodiment of FIG. 1 wherein like elements are designated by like numerals, where appropriate.

The piezo-electric transducer 12 is coupled to the gate of an FET Q6 which has a very high input impedance and is substantially immune to a high capacitance input, such as the transducer 12. Low gain FET Q6 is utilized with a standard transistor amplifier including transistor Q7 to provide an amplifier 16 with a gain of one.

The output of amplifier stage 16 is fed to a low pass amplifier stage 18 having a gain of the order of between thirty and forty and providing a low pass frequency of the order of ninety-five Hertz.

As shown in FIGS. 2-1 and 2-2 the transducer 12 is coupled between ground potential and gate G of FET transistor Q6 which is immune to a high capacitance input and has a high input impedance. The FET Q6 is coupled to transistor Q7 which, cooperatively with Q6, provides a gain of one. The collector of Q7 is coupled through capacitor C8 to the inverting input of the combined amplifier low pass filter stage 18 comprised of gain amplifier U12B. High frequency signals are coupled through the output of U12B back to the inverting input through capacitor C11 which serves to feed back and cancel high frequency signals. The low pass filter passes signals under 100 Hertz. The output of low pass filter/amplifier stage 18 is coupled to amplifier circuit 20 comprised of amplifier U8C which provides a gain of three to one. The output of stage 20 is coupled to stage 20' which includes amplifier U8D and serves to amplify and invert the output of amplifier 20. The output of inverter stage 20' is coupled to peak detector 22 which charges capacitor C6. Diodes D1 and D5 prevent reverse current flow, assuring charging of capacitor C6 to the peak voltage. Bifet gate U7A has its control input U7A-13 coupled to an output of converter U2B. When input U7A-13 goes high, the resistance across terminals U7A-1 and U7A-2 drops to about 100 ohms to discharge capacitor C6. When control U7A-13 is low, the resistance between U7A-1 and U7A-2 is substantially an open circuit. Bifet U7A is utilized to discharge capacitor C6, when appropriate, under control of timing circuit U6 in a manner to be more fully described.

U8A of circuit 22 serves as a buffer amplifier enabling the voltage across capacitor C6 to be coupled to other circuits without discharging the peak value stored by capacitor C6. The output of buffer U8A is coupled to the input U7B-11 of bifet U7B and is further coupled to the non-inverting input differential amplifier U1B and to the inverting input of differential amplifier U1A, which differential amplifiers (46, 48, see FIG. 1) are utilized to control the LED to be illuminated, as will be more fully described hereinbelow.

Calibrate switch S2 is coupled across capacitor C4. Capacitor C4 is coupled between ground potential and VCC1 by resistor R12. Both terminals of NAND gate U5C are coupled to the common terminal between R12 and C4. U5C operates as an inverter. C4 is normally fully charged, placing a high level at the inputs of U5C and maintaining its output low. When switch S2 is closed, C4 is discharged causing a low input at U5C which causes its output to go high. The output of NOR gate U10B is normally high causing the output of NAND gate U5D to go low, through gate U10B. The output of U5D is coupled to one input of NAND gate U3A. NAND gates U3A and U3B form a set/reset flip-flop. The low output at U5D causes the output of U3A to go high which resets the set/reset flip-flop. The high output of U3A is coupled to the control electrode U7B-12 of bifet U7B, coupling the peak voltage level across C6 to U7B through U8A and applying this level through R1 to the inverting input of U9B which compares the peak voltage stored by C6 with the analog voltage, as will be more fully described hereinbelow.

The free running oscillator 32 is comprised of C1, U2A and R4. The output of oscillator 32 is coupled to one input of NAND gate U5B and to the clock input of counter 36 (U6). The Q11 and Q13 outputs of counter 36 are coupled to respective inputs of NAND gates U3C. The counter 36 serves as a timing circuit, Every five seconds, the inputs of U3C go high causing the output to go low. The low output of U3C causes capacitor C7 to discharge through diode D6. C7 is normally fully charged, causing the output of inverter U2B to be normally low. When C7 discharges through D6, the output of U2B goes high. This high condition is passed by NOR gates U11B and U11A to reset counter 36. This resetting operation is continuously repeated at the aforementioned five second interval. If desired, the time interval may be larger or smaller depending upon the requirements of the particular application.

Counter 36 is also reset by operating calibrate initiate switch S2. As was described hereinabove, when switch S2 is closed, the output of U5C goes high, which condition is coupled through Q3, U11B and U11A to reset counter 36 and thereby initiate a calibrate sequence. A high level at U5C caused by closure of switch S2 also resets the set/reset flip-flop comprised of NAND gates U3A and U3B. The output of U3A thus goes high, enabling clock pulses from free running oscillator 32 to be passed by NAND gate U5B to apply clock pulses to the clock input of counter U4. A digital-to-analog circuit comprised of the resistor network of 680K through 10K resistors, coupled respectively to the Q1 through Q7 outputs of counter 36, develop an analog voltage across resistor R3 which is applied to the non-inverting input of a buffer stage U9A whose output is coupled to the non-inverting input of differential comparator U9B. When the analog voltage developed by resistor network 40 is equal to the value stored across capacitor C6 of peak detector circuit 22, the output of differential comparator U9B goes high, causing the output of NOR gate U11C to go low, which state is applied to one input of gate U3B, forming the set/reset flip-flop, causing the output of U3B to go high. This high level is applied to one input of U3A. The other input to U3A is the output of U5D which is normally high, causing the output of U3A to go low and thereby blocking output pulses of free running master oscillator 32 from being applied to the clock input of up counter 36. The low output of U3A is also applied to the control gate U7B-12 of bifet U7B, decoupling the peak voltage level developed across C6 from the input of U9B. Thus, the reference level in binary form is stored within counter 36 and the analog value thereof is constantly made available to the non-inverting input of differential comparator U9B unless and until another calibrate operation is performed.

As was mentioned hereinabove, counter 22' (i.e. counter U6) enables gate U3C every five seconds. Inverter U2B, in addition to applying a pulse to reset counter 22' through gates U11B and U11A, also applies a control input to control terminal U7A-13 of bifet U7A, discharging the charge across capacitor C6 to ground through U7A. Upon the occurrence of the next pulse generated by transducer 12, capacitor C6 is again charged to a peak value. Thus, a new peak value is stored every five (5) seconds.

The voltage value stored across C6 is applied through the output of buffer U8A simultaneously to the non-inverting input of differential comparator U1B and to the inverting input of differential comparator U1A. The analog output developed by resistor network 40 is coupled through buffer amplifier U9A to a voltage divider (44, see FIG. 1) circuit comprised of resistors R57, R54 and R55 coupled in series between the output of U9A and ground potential. A voltage at the GRN/YEL voltage divider terminal is coupled to the inverting input of U1B. A dividing voltage appearing at the YEL/RED terminal between R54 and R55 is coupled to the non-inverting input of U1A. When the stored, divided-down peak value is greater than the reference value, differential comparator U1B, which serves as a lamp selector, applies a high enable input to NAND gate U3D. The other input of U3D is derived from a pulsing circuit (Schmitt trigger) coupled to the output of U12B and comprised of amplifier U12A whose output is coupled through capacitor C10 to the gate electrode of transistor Q8. The circuit (Schmitt trigger) including U12A develops a pulse at a given limit voltage which pulse is applied through C10 and Q8 simultaneously to an associated input of each of the gates U3D, U5A and U10A. In the example given, when the peak level developed across C6 is greater than the reference level, U1B goes high to provide a high level to one input of U3D. The pulse generated by U12A is provided as a high level pulse applied through Q8 to the other input of U3D causing the output of U3D to pulse at the patient's systolic rate. This pulsing output is coupled through R25 to the green LED D2 by selectively switching Q4 on and off.

When the peak voltage stored in peak detector 22 is less than the reference voltage, the output of U1B goes low. This output is inverted through inverter U2D to apply a high input to gate U10A. In a similar manner, when the peak voltage is higher than the reference voltage at the YEL/RED voltage divider terminal, the output of U1A goes low. This output is inverted by inverter U2C providing a high output at the second input of U10A. The third input of U10A is derived from the pulsing circuit and is applied thereto by Q8. Gate U10A thus develops a pulsing output which switches Q1 on and off causing the yellow LED D3 to flash.

When the peak voltage stored in peak detector 22 is lower than the reference voltage, the output U1A goes high. This high level output, plus the pulsing signal appearing at the collector Q8 are respectively applied to the input terminals of U5A to develop a pulsing output. This pulsing output selectively switches Q5 on and off to flash the red LED D4.

Figure 3:
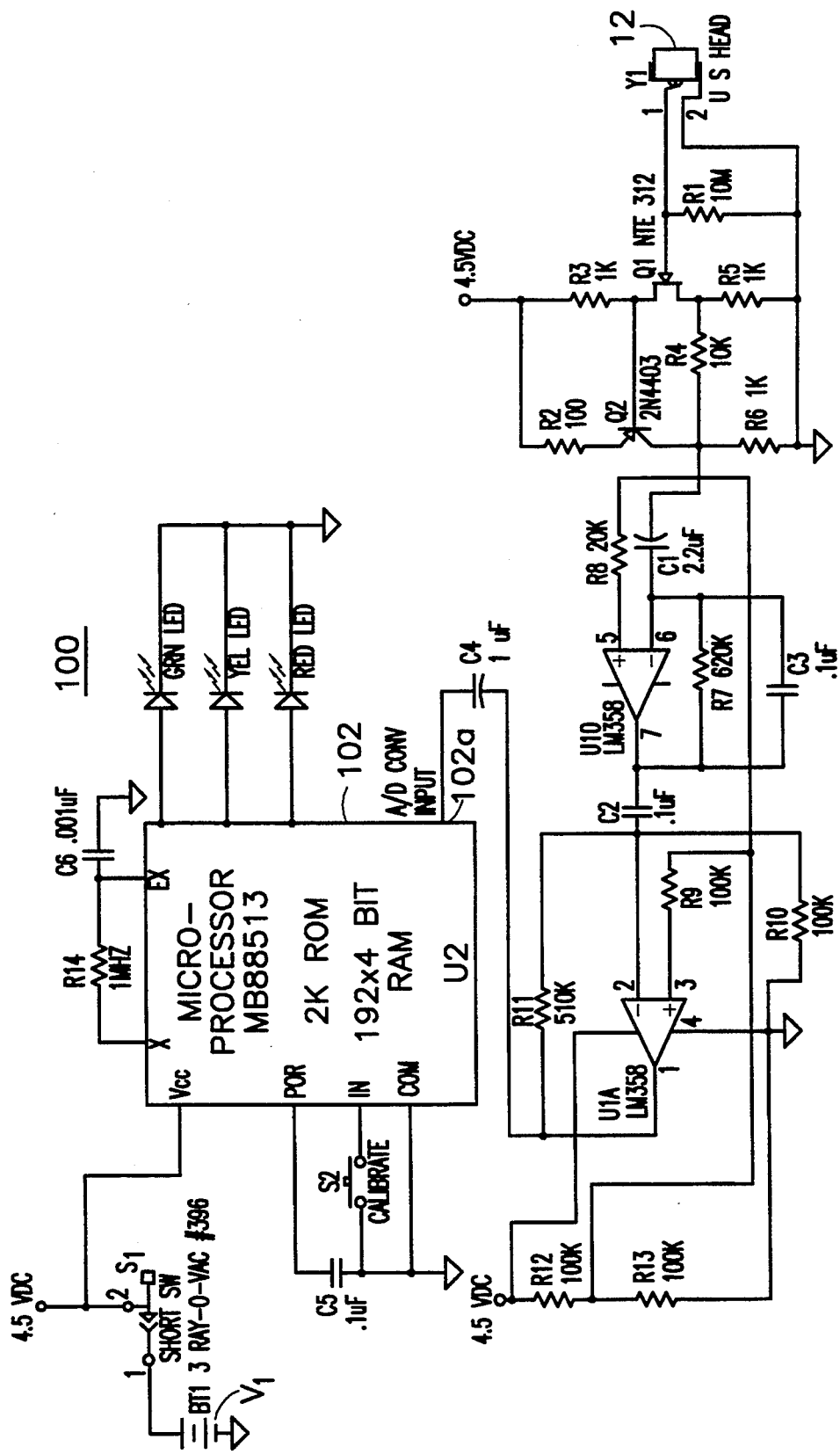
FIG. 3 shows a schematic diagram of a microprocessor-based embodiment of the present invention.

FIG. 3 shows an alternative blood flow monitor embodiment 100 utilizing a microprocessor 102. The battery V1 is coupled to the Vcc input of microprocessor 102 through switch S1. The calibrate switch S2 is coupled to the IN input of the microprocessor.

Transducer 12, which operates in a manner similar to that shown in FIG. 1, has its output coupled to gate G of FET Q1. Q1 and Q2 together form an amplifier with a gain of one. FET Q1 has a high input impedance and is substantially immune to inputs having a large capacitance. The output of Q2, taken from its collector, is coupled to the low pass filter stage U1B which is similar to that shown in FIG. 2. High frequency signals appearing at the output of U1B are coupled back through the input by the RC circuit of R7 and C3 and are cancelled thus providing a low pass filter. An additional amplifier stage including amplifier U1A provides further gain to the input signal and applies the input signal to an A/D converter input 102a of microprocessor 102 through C4. Resistor R14 and capacitor C6 determine the operating frequency of the microprocessor, which is typically one MHz. The microprocessor selectively pulses one of the green, yellow and red LEDs D1 through D3 respectively in a manner similar to the embodiment of FIGS. 1 and 2 in order to provide a flashing indication of the proper color to indicate the blood flow rate through the artery being monitored.

Figure 4:
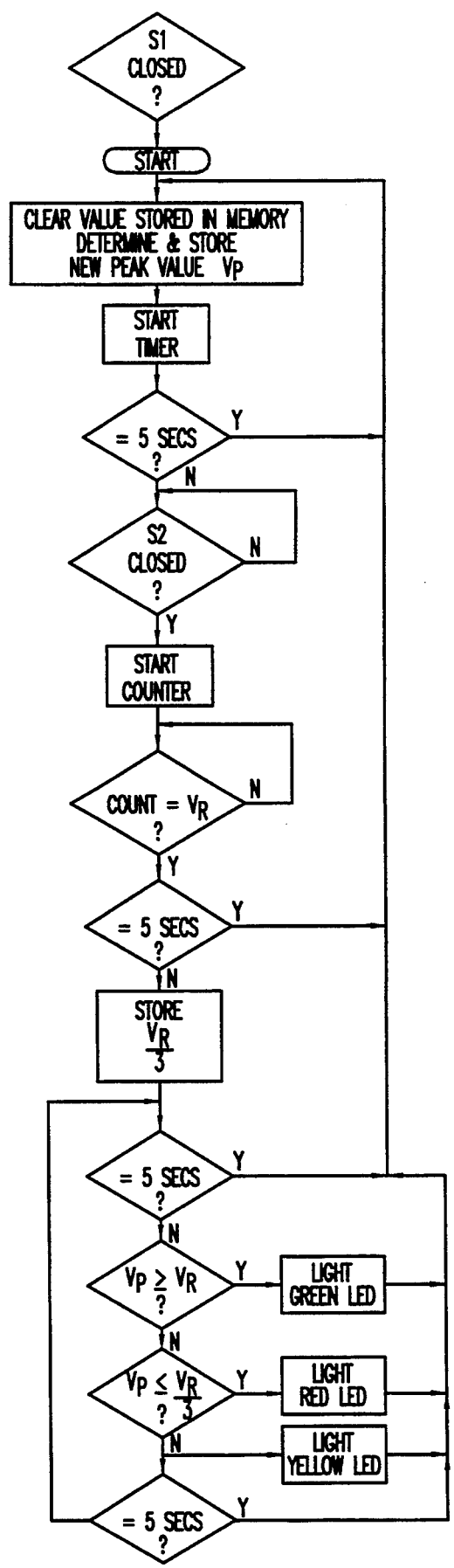
FIG. 4 shows a flow diagram useful in explaining the manner of operation of the embodiment of FIG. 3.

FIG. 4 shows a flow diagram of the microprocessor-based monitor 100.

FIGS. 5a and 5b show top plan and side elevational views respectively of the combined transducer and electronics of one of the embodiments shown in either FIG. 1 or FIG. 3. The transducer 12 is mounted upon a thin metallic plate 14 and is embedded within a molded silicone housing 112. The "+" reference mark R provided immediately above transducer 12 serves as a locating "cross-hair" to aid in positioning the transducer at a location upon the patient's body and above the artery at a location where a suitable deflection signal is obtainable.

The electronics (see FIGS. 1, 2 or 3) is also mounted on substrate 14 a spaced distance from transducer 12 and is likewise embodied within the molded silicone case. The arcuate slots 112a, 112b facilitate bending of the substrate 14. A suitable lead (not shown) is coupled between transducer 12 and the monitor electronics and is likewise embedded in the molded silicone housing 112 and extends between transducer 12 and the electronics 100, for example. Conductive plate 14 serves as the other electrical connection between transducer 12 and the control circuitry. The LEDs D1, D2 and D3 are viewable from the top surface of the monitor through suitable openings. The underside of member 14 is coated with a suitable adhesive gel which is chosen to provide satisfactory adhesion for the monitor so that the monitor and specifically the transducer will not undergo any displacement from the desired position above the artery during the operating period, which is typically of the order of fifty hours. The adhesive layer 114 is covered with a release sheet 116 which is peeled away preferably immediately preparatory to positioning on the patient's body.

Figure 7A:
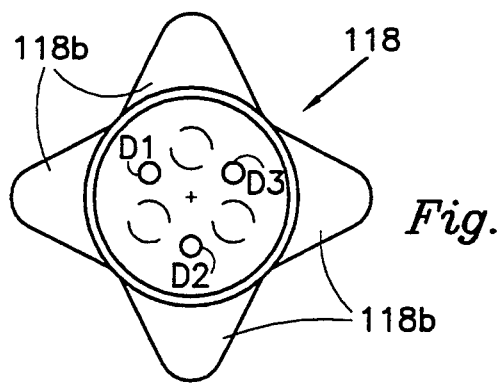
Figure 6A:
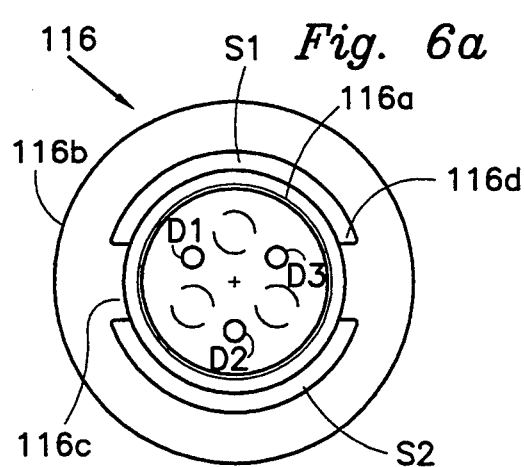
Figure 8A:
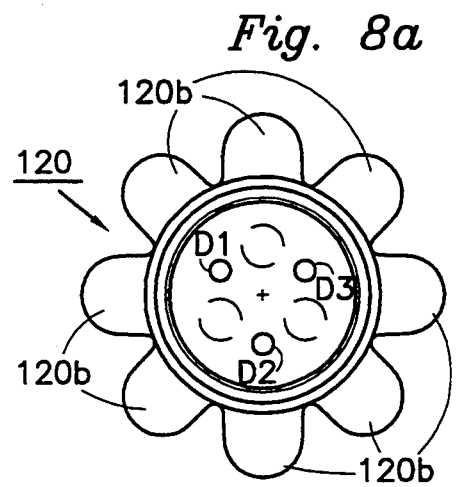

FIGS. 6a, 7a and 8a show further alternative embodiments of the present invention in which the system electronics is mounted immediately above the transducer 12.

FIG. 6a shows transducer 12 mounted upon plate 14. The molded silicone housing covers the system electronics and provides three windows for viewing the LEDs D1 through D3. The molded silicone housing 116 is further provided with a ring-shaped flange 116b joined to the portion 116a of housing 116 which encloses the electronic module 100 and is partially separated therefrom by a pair of radial sections 116c, 116d providing a pair of arcuate-shaped slots S1 and S2, to facilitate bending of the center portion of substrate 14. The undersurface of the mounting plate 14 and the undersurface 116e of ring-shaped flange 116b is coated with the aforementioned adhesive gel.

Figure 7B:
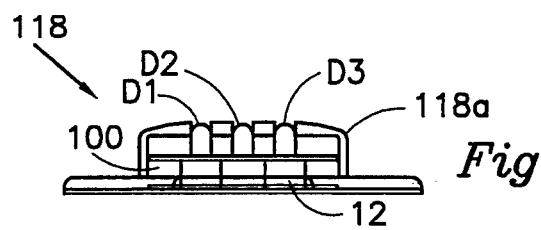

In the embodiment of FIGS. 7a and 7b, the molded silicone housing 118 has a central portion 118a encapsulating the system electronics 100 and partially encapsulating the LEDs D1, D2 and D3 and providing "windows" for visual observation. The molded silicone housing is provided with a plurality of integral, substantially triangular-shaped projections 118b having curved tips. The undersurface of the structure shown in FIG. 7b is coated with the aforementioned adhesive gel, including the undersurface of projections 118b.

Figure 8B:
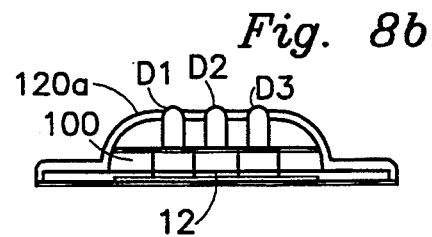

In the embodiment of FIGS. 8a and 8b, the molded silicone housing 120 has a central portion 120a encapsulating the transducer 12, electronics 100 and partially encapsulating the LEDs D1, D2 and D3 while providing windows to permit their visual observation. The silicone housing 120 is further provided with integral projections 120b extending radially outwardly. The undersurface of the central portion and projections 120b of the embodiment shown in FIGS. 8a and 8b is coated with the aforementioned adhesive gel in order to adhere the monitor to the skin of a patient.

Figure 6B:
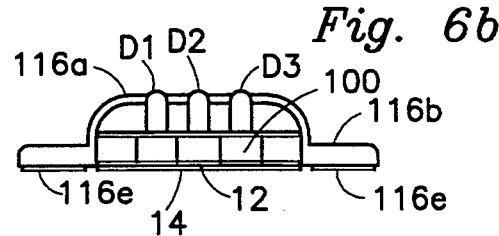

Incidentally, the embodiments of FIGS. 6 through 8 are properly located by positioning their centers above the desired artery. A suitable centering reference symbol. R such as the "+" shown in FIG. 6a may be utilized for this purpose.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein described.

What is claimed is:

1. Monitor means for monitoring flow through a vessel by measuring deflection of said vessel during flow, comprising:
    a substrate having one major surface adhered to a surface in close proximity to said vessel being monitored;
    said substrate comprising a thin, conductive, metallic plate capable of being deflected responsive to a deflection of said vessel wall;
    control circuitry including:
    transducer means mounted upon said substrate for generating an electrical signal responsive to deflection of said substrate;
    peak detector means responsive to energization of said monitor means for periodically and repetitively determining a peak value of each deflection responsive to an output of said transducer means;
    reference generating means responsive to operation of a calibrate switch for storing a peak value of a deflection for use as a reference value;
    means for comparing said stored value with each value periodically determined by said peak detector means; and means for providing a visually readable indication of said comparison.

2. The monitor means of claim 1 further comprising low pass filter means for assuring that the output of the transducer means applied to said peak detector is limited to a predetermined type of pulses.

3. The monitor means of claim 2 wherein said predetermined type of pulses comprise systolic pressure pulses.

4. The monitor means of claim 1 further comprising low pass filter means for filtering out unwanted frequencies from the output of the transducer means.

5. The monitor means of claim 1 wherein said peak detector means includes a sample-and-hold circuit means.

6. The monitor means of claim 1 wherein said peak detector means comprises timing means for clearing a peak value stored therein after a predetermined time interval to enable storage of a peak value of a subsequent deflection signal derived from said transducer means.

7. The monitor means of claim 6 wherein said timing means includes means for providing a time interval sufficient to assure the receipt of at least one deflection signal by said peak detector means during said time interval.

8. The monitor means of claim 1 wherein said reference generating means further comprises:
    free running oscillator means;
    means for accumulating output pulses from said free running oscillator means responsive to operation of said calibrate switch;
    digital-to-analog means for converting said count in said accumulating means to an analog value; and
    means for comparing said analog value with a value stored in said peak detector means for preventing further accumulation of output pulses from said free running oscillator means by said counter means when said analog value equals the value stored in said peak detector means.

9. The monitor means of claim 8 further comprising voltage divider means for dividing the output of said digital-to-analog converter means into a plurality of voltage reference levels;
    said visual display means further comprising means for comparing each value stored by said peak detector means with said reference value for generating one of a plurality of visually observable output conditions representative of the value stored in said peak detector means relative to said reference value.

10. The monitor means of claim 9 wherein said visual display means comprises a plurality of light emitting devices selectively illuminated according to the value stored by said peak detector means relative to said reference value.

11. The monitor means of claim 8 wherein said digital-to-analog means further comprises a resistor network for converting the binary output of said accumulating means into an analog voltage level.

12. The monitor means of claim 1 wherein said transducer means comprises a piezo-ceramic disc.

13. The monitor means of claim 1 wherein said transducer means comprises a lead-zirconate-titanate unimorph piezo-ceramic disc.

14. The monitor means of claim 13 wherein said piezo-ceramic disc is a crystal which is electrically polarized in the 33 direction.

15. The monitor means of claim 1 wherein said calibrate switch comprises a semi-hidden control switch operated by a tapered point of an instrument.

16. The monitor means of claim 1 further comprising encapsulating means incorporating an insulating material for encapsulating said control circuitry, said transducer means being mounted upon said one major surface of said substrate, and the remainder of said control circuitry being mounted on a second major surface of said substrate opposite said one major surface.

17. The monitor means of claim 16 wherein said encapsulating means comprises a silicone gel.

18. The monitor means of claim 1 further comprising an insulating material for encapsulating said control circuitry and said transducer means;
    said transducer means and the remainder of said control circuitry being mounted displaced from one another on a second major face of said substrate opposite said one major face.

19. The monitor means of claim 18 wherein said encapsulating means comprises a silicone gel.

20. The monitor means of claim 1 wherein said substrate comprises a thin, flexible, conductive plate which provides a mechanical advantage to deflections of said vessel.

21. The monitor means of claim 20 wherein said plate is a brass plate.

22. Monitor means for monitoring flow through a vessel by measuring deflection of said vessel during flow, comprising:
- a substrate having one major surface adhered to a surface in close proximity to said vessel being monitored;
- said substrate comprising a thin plate capable of being deflected responsive to a deflection of said vessel wall;
- control circuitry including:
- transducer means mounted upon said substrate for generating an electrical signal responsive to deflection of said substrate;
- peak detector means responsive to energization of said monitor means for periodically and repetitively determining a peak value of each deflection responsive to an output of said transducer means;
- reference generating means responsive to operation of a calibrate switch for storing a peak value of a deflection for use as a reference value;
- means for comparing said stored value with each value periodically determined by said peak detector means; and
- means for providing a usually readable indication of said comparison.

23. The monitor means of claim 22 wherein said thin plate has conductive properties.

* * * * *